United States Patent [19]

Baba

[11] 4,433,692
[45] Feb. 28, 1984

[54] ULTRASONIC DIAGNOSIS DEVICE
[75] Inventor: Kazuo Baba, Tokyo, Japan
[73] Assignee: Olympus Optical Co., Ltd., Tokyo, Japan
[21] Appl. No.: 377,024
[22] Filed: May 11, 1982
[30] Foreign Application Priority Data
  May 20, 1981 [JP]  Japan .................................. 56-76079
[51] Int. Cl.³ .............................................. A61B 10/00
[52] U.S. Cl. ........................................ 128/660; 128/6
[58] Field of Search ............................ 128/660, 4-8
[56] References Cited
U.S. PATENT DOCUMENTS

| 2,583,437 | 1/1952 | Fossati | 128/4 |
| 3,835,841 | 9/1974 | Terada | 128/5 |
| 3,918,438 | 11/1975 | Hayamiju et al. | 128/4 |
| 4,212,207 | 7/1980 | Conradi | 73/623 |
| 4,375,818 | 3/1983 | Suwaki et al. | 128/4 X |

FOREIGN PATENT DOCUMENTS

| 53-85982 | 7/1978 | Japan | 128/660 |
| 55-42674 | 3/1980 | Japan | 128/660 |

Primary Examiner—Kyle L. Howell
Assistant Examiner—Francis J. Jaworski
Attorney, Agent, or Firm—Frishauf, Holtz, Goodman & Woodward

[57] ABSTRACT

An ultrasonic wave diagnosis device includes an ultrasonic wave transmission/reception scanner disposed at a distal end of an insertion section and having an ultrasonic wave oscillator therein, and a balloon surrounding the scanner and inflated outwardly by supplying an ultrasonic wave propagation liquid medium. A recess is formed in part of a circumferential surface of the insertion section, in the vicinity of the balloon in which an observation optical system is disposed to have a field of sight toward the balloon.

2 Claims, 4 Drawing Figures

ULTRASONIC DIAGNOSIS DEVICE

BACKGROUND OF THE INVENTION

The present invention relates to an ultrasonic diagnosis device having an endoscope which is inserted into a body cavity.

An ultrasonic wave transmission/reception scanner of this type must be in tight contact with the wall of the body cavity which is scanned with the ultrasonic wave during a diagnosis. As shown in FIG. 1, an ultrasonic transmission/reception section 2 at the distal end of an insertion section 1 is surrounded by an inflatable balloon 3 which is filled with an ultrasonic wave propagation liquid medium. The ballon 3 is inflated and brought into contact with the wall of the body cavity to transmit the ultrasonic wave. However, in addition to the ultrasonic wave transmission/reception section 2, an observation optical system 4 is also mounted at the distal end of the insertion section 1. When the balloon 3 comes in tight contact with the wall of the body cavity, the observation optical system 4 may come closer to the wall or may come in tight contact with the wall, thus impairing observation.

In order to eliminate the above drawback, a link mechanism is used to arrange the ultrasonic wave transmission/reception section 2 to be movable parallel to the observation optical system 4. While ultrasonic wave diagnosis is performed, only the ultrasonic transmission/reception section 2 is extended parallel to the observation optical system 4 and is then brought into tight contact with the wall of the body cavity. Then, the field of sight is assured since the observation optical system 4 is sufficiently apart from the wall. However, a mechanism for moving the ultrasonic wave transmission/reception section 2 becomes complex and the distal end portion of the insertion section becomes large, resulting in high cost. Further, operability of the device is degraded.

SUMMARY OF THE INVENTION

The present invention has been made in consideration of this and has for its object to provide an ultrasonic wave diagnosis device, at low cost, having a simple structure to assure a field of sight of an observation optical system and a compact distal end portion of an insertion section with excellent operability.

BRIEF DESCRIPTION OF THE DRAWINGS

FIG. 2 to FIG. 4 show an ultrasonic wave diagnosis device according to one embodiment of the present invention, in which FIG. 2 is a side view of the ultrasonic wave diagnosis device, FIG. 3 is a sectional view of a distal end portion thereof, and FIG. 4 is a plan view of an observation optical system.

DETAILED DESCRIPTION OF THE PREFERRED EMBODIMENT

Figure 1:
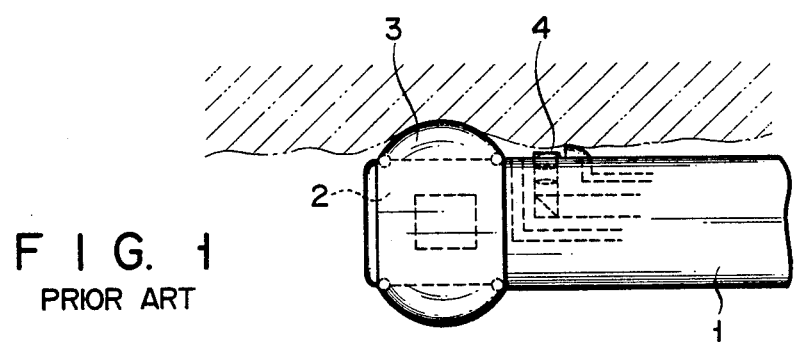
FIG. 1 is a side view of a distal end portion of a conventional ultrasonic wave diagnosis device.
Figure 2:
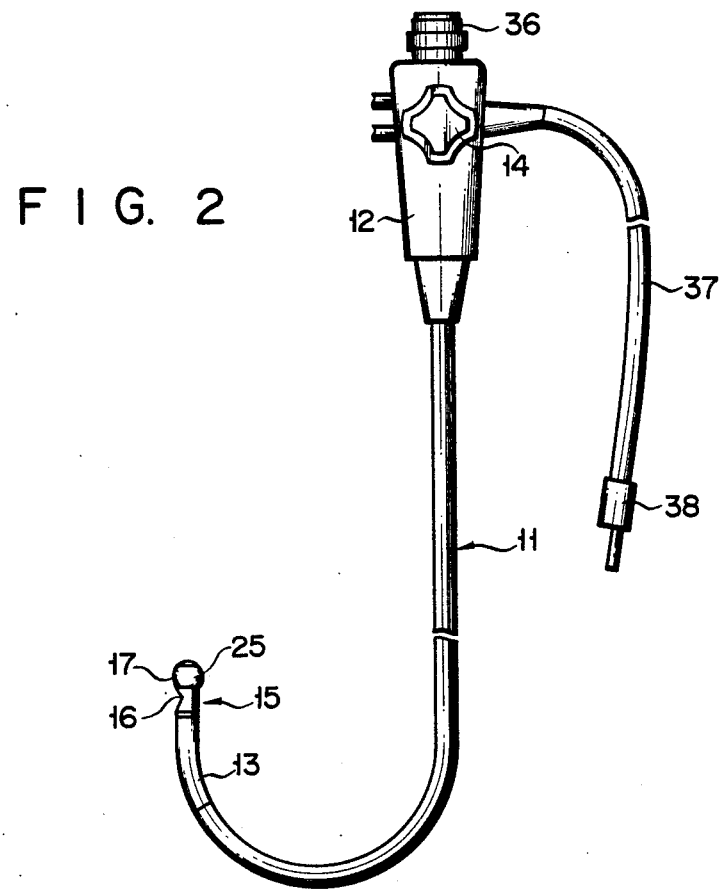
Figure 3:
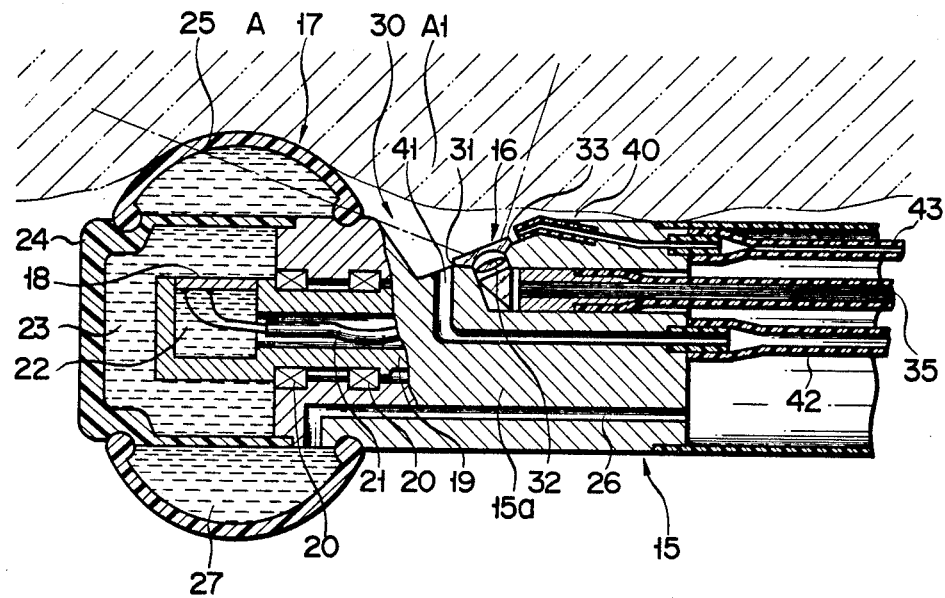
Figure 4:
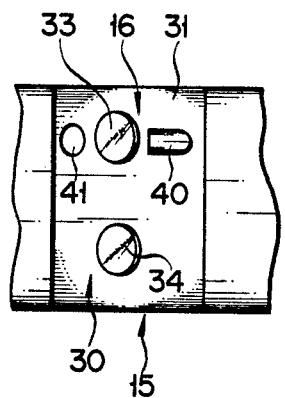

An ultrasonic wave diagnosis device according to one embodiment of the present invention will be described hereinafter with reference to FIGS. 2 to 4. A flexible elongate insertion section 11 is inserted into a body cavity. The proximal end of the insertion section 11 is connected to a control section 12. A flexible bending portion 13 is connected to the distal end of the insertion section 11. The flexible bending portion 13 can be arbitrarily bent at a desired curvature by rotating a control knob 14 disposed at the control section 12 through a transmission wire (not shown).

An observation optical system 16 and an ultrasonic wave transmission/reception scanner 17 are mounted at a distal end section 15 of the bending portion 13. The ultrasonic wave transmission/reception scanner 17 houses an ultrasonic wave oscillator 18, as shown in FIG. 3. The ultrasonic wave oscillator 18 is arranged within a recess formed in the circumferential surface of the distal end section of a cylindrical shaft 19 extending along the insertion section 11. The ultrasonic wave oscillator 18 is rotated integrally with the shaft 19 in the circumferential direction of the distal end section 15. The shaft 19 is coaxially inserted through a cylindrical distal end assembly member 15a made of metal. The shaft 19 is rotatably supported by a pair of bearings 20 which are arranged at a interval on the inner wall of the member 15a. The shaft 19 is then rotated by a driving shaft (not shown). A signal line 21 which is connected to the ultrasonic wave oscillator 18 transmits the ultrasonic wave signal. A damper 22 is filled in the recess formed in the distal end part of the shaft 19. The damper 22 absorbs the ultrasonic wave transmitted behind the ultrasonic wave oscillator 18. An ultrasonic wave propagation liquid medium 23 is filled in a hollow chamber formed at the distal end of the distal end assembly member 15a and surrounds the ultrasonic wave oscillator 18. The opening of the hollow chamber of the distal end assembly member 15a is closed by a plastic cap 24, so that the liquid medium 23 is sealed therein.

A balloon 25 has a spherical section to surround the ultrasonc transmission/reception scanner 17. The balloon 25 made of an elastic material is expandable. The end portion of the balloon 25 is attached to the circumferential surface of the terminal end assembly member 15a. An ultrasonic wave propagation liquid medium 27 is fed to and drawn from a liquid tight chamber at the hollow distal end through a liquid path 26. Thus, the balloon can be inflatable.

A V-shaped recess 30 is formed in the distal end assembly member 15a by partially cutting the circumferential surface thereof and is located in the vicinity of the outer end of the balloon 25. One side surface of the V-shaped recess 30 which is located on the side of the ultrasonic wave transmission/reception scanner 17 has a tilt angle larger than the other side surface 31 of the V-shaped recess 30 with respect to the central axis of the insertion section 11. The observation optical system 16 is disposed on the side surface 31. The observation optical system 16 comprises optical members such as an observation window 33 having an objective lens 32 and an illumination window 34 (FIG. 4). An incident end of a image guide 35 using an optical fiber or the like faces the objective lens 32 and an output end thereof is connected to an eyepiece 36 (FIG. 2) through the insertion section 11. An output end of a light guide (not shown) faces the inner side of the illumination window 34. The incident end of the light guide can be connected to a light source device (not shown) through a universal cord 37 and a connector 38, as shown in FIG. 2.

An air/water supply nozzle 40 and a suction port 41 are connected to a channel tube 42 and draws air/water therethrough. The air/water supply nozzle 40 is connected to a tube 43 which is then connected to an air/water supply source.

In the ultrasonic wave diagnosis device with the above arrangement, the insertion section 11 is inserted in a body cavity while the balloon 25 is being contracted. The user observes the body cavity through the observation optical system 16 and positions the ultrasonic wave transmission/reception scanner 17 to a portion A to be examined. The ultrasonic wave propagation liquid medium 27 is supplied to the balloon 25 through the liquid path 26 to inflate the balloon 25. The control knob 14 is controlled to bend the bending portion 13 and to bring the balloon 25 into tight contact with the portion A. Thus, the ultrasonic wave can be transmitted. An ultrasonic wave drive device (not shown) drives the ultrasonic wave oscillator 18 to rotate it about the shaft of the distal end section 15. The ultrasonic waves thus transmitted are reflected by the tissue of the portion A. This echo wave is then received by the ultrasonic wave oscillator 18 and transmitted to a display unit (not shown) through the signal line 21 and an image processing device. Thus, a tomographic image by the ultrasonic wave is displayed. If the user wish to contract the balloon 25, the ultrasonic wave propagation liquid medium 27 is discharged through the liquid path 26.

As described above, while ultrasonic wave diagnosis is performed, the balloon 25 is in tight contact with the portion A and a wall Al of the body cavity adjacent to the portion A comes close to the circumferential surface of the distal end section 15. Further, since the observation optical system 16 is arranged in the recess 30 formed in the vicinity of the balloon 25 according to the ultrasonic wave diagnosis device of the present invention, the wall Al of the body cavity may not be brought into tight contact with the observation optical system 16, assuring the sufficient field of sight. As described above, the observation window 33 and the illumination window 34 are provided on the side surface 31, so that the balloon 25 is easily brought into the field of sight. As a result, the user can clearly observe the portion A.

The positioning of the balloon to the portion A, that is, orienteering operation is easily performed. Simultaneously, the surface condition of the portion A is constantly observed, so that the user can perform ultrasonic diagnosis properly.

In the above embodiment, the observation optical system is disposed on the side surface 31 which is slightly inclined at any angle toward the balloon. However, the tilt forward may be adopted. In this case, the user can easily observe the balloon within his sight. Thus, the tilt surface may not necessarily be formed.

In summary, the recess is formed at the side surface of the distal end section in the vicinity of the balloon and the observation optical system is arranged in the recess. Therefore, a complex mechanism for moving the ultrasonic wave transmission/reception scanner relative to the observation optical system is not required. Thus, the field of sight for the observation optical system of the ultrasonic wave diagnosis device is assured only by the formation of the recess. The ultrasonic wave examination device of the present invention is of low cost, is simple to construct and provides the field of sight for stable observation with simple operation. Further, the distal end of the insertion section is not large in size, resulting in a compact distal end section.

What is claimed is:

1. An ultrasonic wave diagnosis device comprising:
   an insertion section having one end which is insertable into a body cavity, another end which is located outside the body cavity, and a central axis;
   a control section connected to said another end of the insertion section;
   an ultrasonic wave transmission/reception scanner disposed at said one end of the insertion section and having an ultrasonic wave oscillator therein;
   a balloon inflatable toward the outside and surrounding said ultrasonic wave transmission/reception scanner disposed at said one end of the insertion section;
   means disposed in said insertion section for supplying an ultrasonic wave propagation liquid medium to the balloon disposed in said insertion section to inflate the balloon;
   said insertion section having a recess formed in part of a circumferential side surface thereof, which is in the vicinity of said balloon; and
   an observation optical system disposed within the recess and having a field of sight toward the balloon, said observation optical system including an observation window and an illumination window; and
   said recess having one inner surface which is inclined toward the central axis of the insertion section from the insertion section to the balloon such that said inclined inner surface of the recess is inclined toward the balloon, and said observation optical system being disposed in said one inclined inner surface of said recess.

2. A device according to claim 1, wherein said recess further includes another inner surface which is inclined to be apart from the central axis of the insertion section from the insertion section to the balloon the angle of inclination of said another inner surface of said recess being larger than the angle of inclination of said one inner surface of said recess in which said observation optical system is disposed.

* * * * *